United States Patent [19]
Grant

[11] Patent Number: 5,653,741
[45] Date of Patent: Aug. 5, 1997

[54] HEATING AND COOLING PAD

[76] Inventor: Edward F. Grant, 7347 Panache Way, Boca Raton, Fla. 33433

[21] Appl. No.: 518,035

[22] Filed: Aug. 22, 1995

[51] Int. Cl.$^6$ .................................................. A61F 7/00
[52] U.S. Cl. ............................................. 607/114; 607/96
[58] Field of Search ................................... 607/114, 112, 607/104–105, 96, 108–111

[56] References Cited

U.S. PATENT DOCUMENTS

| | | |
|---|---|---|
| 3,894,213 | 7/1975 | Agarwala . |
| 4,042,803 | 8/1977 | Bickford . |
| 4,782,601 | 11/1988 | Gonzalez . |
| 4,860,748 | 8/1989 | Chiurco et al. ............... 607/96 |
| 4,937,435 | 6/1990 | Goss et al. . |
| 5,097,829 | 3/1992 | Quisenberry . |
| 5,174,285 | 12/1992 | Fontenot . |
| 5,184,612 | 2/1993 | Augustine . |
| 5,431,622 | 7/1995 | Pyrozyk et al. ............ 607/114 X |

*Primary Examiner*—Lee S. Cohen
*Assistant Examiner*—Ryan Carter
*Attorney, Agent, or Firm*—Miller, Canfield, Paddock and Stone

[57] ABSTRACT

A flexible pad capable of selectably heating or cooling an animal or human body part. The pad is formed of two planar surfaces having at least two side portions disposed between said planar surfaces that are made of a mesh material for air circulation within the pad. One planar surface is made of thermal conductive material having a plurality of thermoelectric modules bonded to the conductive material. The thermoelectric modules transfer heat to or away from the conductive material. A heat sink is attached to the opposing side of each modules for dissipating heat from the conductive material during the cooling process. A rheostat has a reversing switch for changing polarity of the rheostat to either transfer heat to the thermoelectric modules and to the planar surface, or from the thermoelectric module to the heat sink.

9 Claims, 2 Drawing Sheets

HEATING AND COOLING PAD

FIELD OF THE INVENTION

The present invention relates to a pad for heating or cooling an animal or human body part.

BACKGROUND OF THE INVENTION

Studies indicate that lowering the body temperature at an injured site can reduce swelling and pain while promoting healing. In many injuries, it is beneficial to the injured site to first lower the temperature for a short period of time, and then to apply heat to the same injured site.

There are various devices that individually provide a means to cool or to heat the injured site. A common technique to cool the affected area is to apply ice, usually in an ice pack. Although ice has the advantage of being inexpensive and readily available, it is not healthy to apply ice to the skin for prolonged periods of time. The temperature of the ice can damage skin if left for more than a few minutes in one area. As a result, ice only cools the upper surface of the skin and deep penetration of the cooling process does not take place.

Another means for localized cooling are cold packs made of two chemicals located in individual membranes. When the membranes rupture and the chemicals are allowed to mix, the mixing process causes an endothermic reaction that provides localized short term cooling. One disadvantage of the chemical cooling pack is that the packs are not reusable.

A more sophisticated means for cooling a body part is disclosed in U.S. Pat. No. 5,097,829 issued to Quisenberry. This device provides a temperature controlled fluid circulating system that controls fluid in a thermal blanket having a thermal electric cooling device wherein the temperature control fluid is cooled by the cold set of the cooling device and pumped through and from the blanket through first and second conduits. The conduits are connected to a sealed blanket formed of opposed sheets of vinyl material which are sealed together and define a plurality of passage ways between the sheets for the circulation of the cooling fluid.

Various heating devices are also available ranging from a heat lamp, a hot pack that is similar to the chemical cold pack discussed supra and a heating pad. The heat lamp has a disadvantage in that it is difficult to focus the heat to only the injured area without affecting surrounding tissue. The hot pack has the disadvantage that it can only be used one time when the membranes rupture and thereby mix the chemicals. A heating pad is disclosed in U.S. Pat. No. 4,042,803 issued to Bickford. The heating pad has flexible material that is adapted to be supported on a human body part, wherein an electrical heating elements are embedded inside the support material. The heating elements are connected to an electrical energy source for selectively heating the part of the body in contact with the sheet of material.

As with all of the aforementioned devices for heating and cooling, each device can only accomplish one activity. As a result, if trauma occurs to a body part that requires both the application of cold and heat to the affected body part, two separate devices are required. Therefore, it is advantageous to provide a device that can selectably provide both cold and heat to a body part. It is also advantageous to provide a device that can be used repeatedly. It is further an object of this invention that the device provides a flexible pad that can be wrapped about an injured portion of the body while providing heat or cold to the affected area. It is further an object of the invention to provide a device that is thermoelectrically controlled. Finally, it is an object of this invention to provide a device that controls and limits the temperature range so that the pad does not get too hot or too cold.

SUMMARY OF THE INVENTION

The current invention addresses the aforementioned objectives by providing a device that selectively transfers heat to or away from the body. The invention provides for a flexible pad which houses heat transfer elements. The heat transfer elements include a plurality of thermoelectric modules which are spaced in a generally parallel layer directly beneath the surface forming the pad. The modules are interconnected to each other and having a common connection to an energizing source. Disposed in line between the energizing connector and the thermoelectric modules is a manually actuated rheostat having a reversing switch that changes the polarity of the rheostat to move heat from one side of the thermoelectric modules to an opposing side of the thermoelectric modules. A thermistor in the form of a thermo disk monitors the heat within the pad and provides a shutoff means if the temperature exceeds a predetermined temperature setting. Small high efficiency fans are also connected to the power supply and located within the pad to provide air circulation and to dissipate heat from the pad when the temperature reaches beyond the predetermined safety temperature setting.

The pad itself includes upper and lower planar surfaces and side surfaces connected therebetween. The upper planar surface is impregnated with conducting fibers in order to even out the heat throughout the upper planar surface. The thermoelectric modules are bonded to the upper surface having the conducting fibers. At least two of the side portions of the pad have mesh material to allow for the circulation of air into and out of the pad.

Other objects, advantages and applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein.

DESCRIPTION OF THE PREFERRED EMBODIMENT

Figure 1:
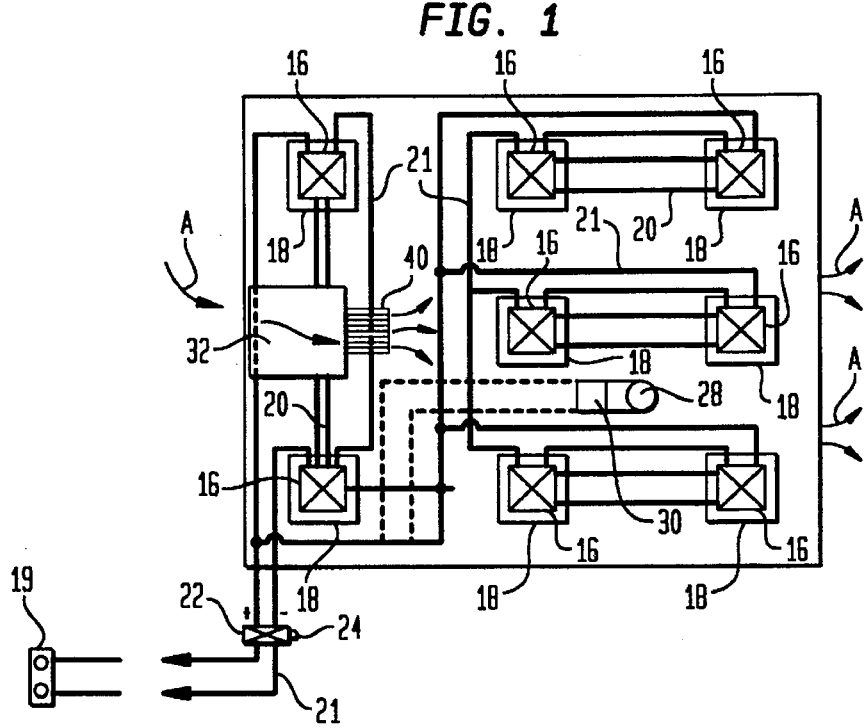
FIG. 1 is a plan view of one embodiment of the heating and cooling device with the cover removed to expose elements of the device.
Figure 2:
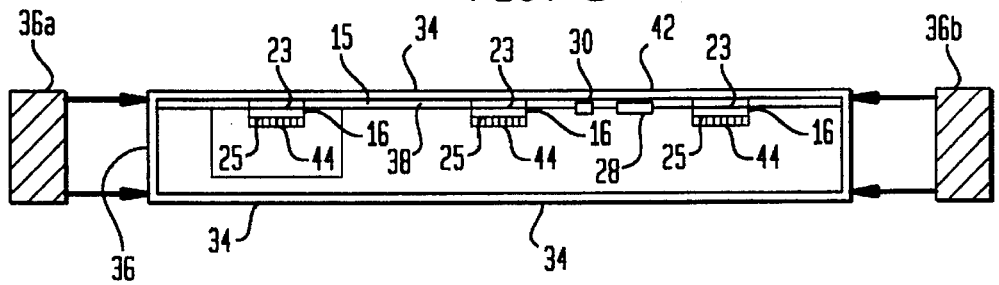
FIG. 2 is a side view of the heating and cooling device of FIG. 1 with the cover attached.

Referring to FIGS. 1–5, the invention is a flexible device 10 designed for therapeutic use to provide heat or cold to the applied body part 12 to alleviate pain and swelling. The device comprises a flexible enclosure 14 housing heat transfer elements as shown in FIG. 1. The heat transfer elements include a plurality of thermoelectric modules 16 that are generally spaced evenly within the area of the enclosure 14. The thermoelectric module 16 is an element that when connected to a direct current power source 19, the current causes heat to move from a first side 23 of the thermal electric module 16 to a second side 25. If the polarity of the direct current reverses, the heat will move back to the first side 23. The number of thermoelectric modules 16 located in the enclosure is determined by the desired therapeutic use of the device 10 and the amount of heat transfer necessary to provide adequate heating and cooling for the body part 12. A thin layer of insulation material 18 surrounds each module 16 to prevent contact between two thermoelectric modules 16 when the enclosure 14 is folded. The device is designed so that at least one outer surface 15 of the enclosure 14 is adjacent or attached to the modules 16. Outer surface 15 is the surface of the enclosure that is placed against the body part 12. As seen in FIG. 2, the first side 23 of each module 16 is adjacent to surface 15.

Flat braided copper 20 or a copper plate is used to connect together some or all of the modules 16. The modules 16 also have a common connection 21 to an energy and voltage source 19 used to supply electrical energy to the heating and cooling enclosure 14. The energizing means may include electrical power supply means of any suitable type and may comprise a rechargeable battery converter or a transformer system for adapting the heating/cooling elements to a commercial power supply or other source of electrical energy. Disposed in the common connection line 21 to the voltage source is an energizing device and a rheostat 22 having a reversing switch 24. Disposed between the heating and cooling device 14 and the rheostat and energizing device may be a connector 13 for selectively attaching the device 14 to the energizing device 22 to provide mobility of the user. The energizing device and rheostat 22 allows the user to control the amount of heating or cooling desired. The reversing switch 24 changes the polarity of the rheostat 22 to provide heat to the first 23 or the second 25 side of the thermoelectric modules 16. When the reversing switch 24 is in a normal position, the electrical current passing through the thermoelectric modules 16 add and move heat to the first side 23 of modules 16. When the reversing switch 24 is in a reverse position, the electrical current is reversed to add and move heat to the second side 25 of the modules. When the reversing switch 24 is in the reverse position, heat is removed from the first side 23 of the modules and thereby cools the first side 23 and the adjacent surface 15.

Figure 5:
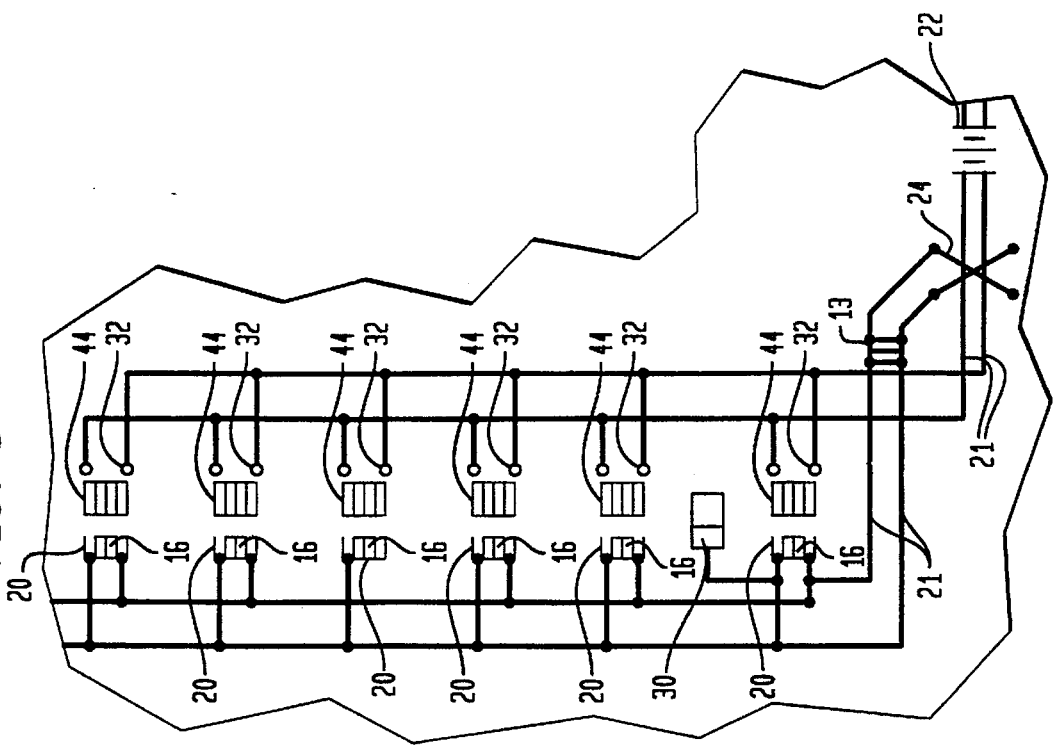
FIG. 5 is a wiring diagram of the preferred embodiment of the heating and cooling device having a plurality of fans.

A thermistor, in the form of a thermal disc 28, is generally centrally located in the enclosure 14 to limit the temperature of the device 10 to prevent overheating and possible injury to the user. A temperature controller 30 is also connected in series with the thermal disc 28 to deactivate the device 10 if the temperature limit is exceeded. In the preferred embodiment, the device will deactivate at 122° F. The device 10 is intended to have a temperature range of 35° F. to 110° F. One or more small fans 32 may also be secured within the enclosure 14 to further circulate air throughout the interior to dissipate the heat. FIG. 1 shows one embodiment of the pad illustrating a single fan 32 for circulating the air. FIG. 5 shows the preferred embodiment of the pad wherein each thermoelectric module 16 has an individual fan 32 for circulating air and dissipating heat. The fans 32 are wired to the power supply before the rheostat 22 so that the fans 32 are not subject to the rheostat reversing switch 24. While power is supplied to the device, the fans 32 are running constantly. The location of fans 32 in the enclosure 14 will be discussed further.

The flexible enclosure 14 is a pad 14 consisting of two flexible planar surfaces 34 and side surfaces 36 disposed between the planar surfaces 34 and connecting the two planar surfaces 34. At least one planar surface 15 of the pad that is to be placed next to the body part 12 is comprised of a heat conducting material 38. The heat conducting material 38 may be formed of a wire material or in the alternative, having carbon, aluminum, or graphite fibers impregnated within and throughout the material. Another layer 42 of material may overlay the heat conducting material 38 to separate the heat conducting material from the user's skin for added comfort. A preferred material is a flexible urethane material. Each of the first sides 23 of the thermoelectric modules 16 having the same polarity are bonded to the heat conducting material 38. The conducting material 38 dissipates the heat from the thermoelectric modules 16 to evenly distribute the heat over the entire surface 15 of the pad.

At least two opposing side surfaces 36a, 36b comprise a semi-rigid mesh type material or a semi-rigid material having a plurality of apertures in the material so that the interior of the pad is provided with an access to atmospheric air to provide adequate air flow through the interior of the pad 14. In FIG. 1, the small fan 32 is located adjacent one mesh side 36a and is used to suck in surrounding outside air to flow through the enclosure and throughout the interior of the pad 14 before exiting through opposite mesh side 36b (as seen by arrows A). Directional fins 40 on fan 32 direct the air flow to the various thermoelectric modules 16 to dissipate excessive heat. In the preferred embodiment of FIG. 5, there is a fan 32 adjacent each thermoelectric module 16 for dissipating heat and providing adequate air flow throughout the interior of the pad 14. The fans 32 are preferably 6–12 volt fans having 4–7 cubic feet per minutes (C.F.M.) capacity. The plurality of fans 32 eliminates the directional fins 40.

To provide cooling of the surface 15 that is placed on the affected body part 12, heat sinks 44 are bonded to the second side 25 of each thermoelectric modules 16. Bonding may be accomplished by thermally conductive paste or tape or by products such as Chromeric Thermatach™. When the reversing switch 24 is set in the reverse position, the current moves the heat in the thermoelectric modules 16 to the second side 25 bonded to the heat sink 44. The heat sink 44 absorbs and removes heat from the first side 23 of thermoelectric modules 16, and thereby cools the conducting material 38 of the pad that is placed next to the affected body part 12.

Therefore, when it is desired to apply heat to the affected body part 12, the pad 14 is placed on the body part 12 such that the outer surface 15 having the heat conducting material 38 is next to the skin or only separated from the skin by the soft overlaying layer 42. The device 10 is connected to the voltage source 19 and the reversing switch 24 is set in the normal position for heating. The user will adjust the rheostat 22 for a desired temperature. The first sides 23 of modules 16 will heat, wherein the conductive material 38 will evenly distribute the heat over the surface 15 of the pad 14. The thermal disc 28 will prevent overheating, while the fan 32 circulates air through the interior of the pad to remove excess heat. If the pad 14 gets beyond a predetermined high temperature, the temperature controller 30 will automatically shutoff the current through connection line 21 to deactivate the heating device 10.

When it is desired to cool the body part, the reversing switch 24 is simply set in the reverse position for cooling. The user will again adjust the rheostat 22 for a desired temperature. The current flow will now move heat to the second side 25 of the modules 16 wherein the heat sinks 44 will absorb the heat and effectively remove heat away from surface 15. Fans 32 will circulate air throughout the enclosure 14 to remove the heat from heat sinks 44 and into the atmosphere.

Figure 3:
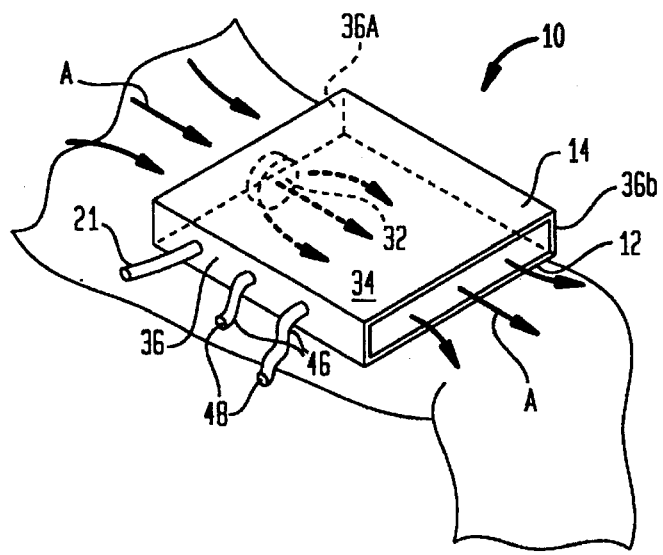
FIG. 3 is a view of the heating and cooling device of the invention in use on a human body leg.
Figure 4:
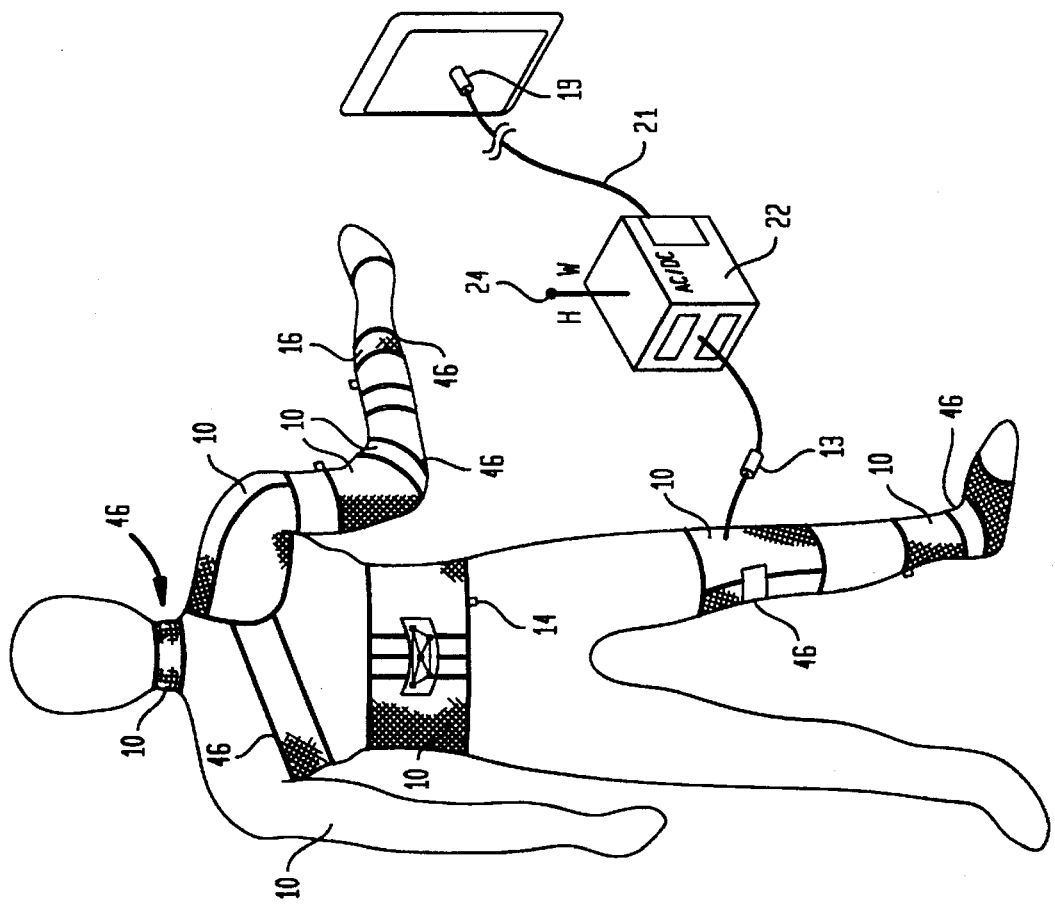
FIG. 4 is a view the heating and cooling device in use on various human body parts.

Although FIG. 3 shows the device 10 being rectangular in shape and being used on a leg, it is within the scope of the invention that the pad 14 can be any shape or size to accommodate various parts of the animal or human body as illustrated in FIG. 4. The material comprising the planar surfaces 34 including the conducting material 38 is flexible and capable of being wrapped around portions of the body 12. To accommodate air circulation in the enclosure, at least two portions of the sides of the pad are made of semi-rigid mesh material which will allow air to enter the enclosure, but will still allow flexibility to wrap the pad 14 around portions of the body 12. To secure pad 14 to the affected area, flexible straps or bands 46 having fastening means 48 such as Velcro® hook and loop fastener snaps or other commonly used fastening means are provided.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A heating and cooling pad, comprising:

first and second planar surfaces made of flexible material and having side insertions disposed between and connecting said first and second planar surfaces; wherein said first and second planar surfaces and side insertions define an enclosure;

a plurality of heat transfer elements each being arranged in the defined enclosure and having first and second sides, said heat transfer elements being thermally insulated from one another and attached to said first planar surface for conducting heat to said first planar surface and dissipating heat from said first planar surface;

thermal coupling means coupled at a first portion thereof to said first side of each of said heat transfer elements and at a second portion thereof to said first planar surface for effecting thermal transfer between said heat transfer elements and said first planar surface;

a heat sink for coupling to said second side of an associated one of said heat transfer elements;

a fan for moving air in the vicinity of one of said heat transfer elements; and actuation means for activating said heat transfer elements in a selectable one of heating and cooling modes of operation, whereby said first planar surface is correspondingly heated or cooled via said thermal coupling means.

2. The heating and cooling pad of claim 1, wherein said first planar surface is impregnated with thermal conductive fibers.

3. The heating and cooling pad of claim 1 wherein the enclosure further comprises at least two opposing side portions made of a semi-rigid mesh material.

4. The thermoelectric heating and cooling pad of claim 3 wherein the fan is located proximate to one of said side portions.

5. The heating and cooling pad of claim 4, wherein said small fan is further provided with directional fins for directing an air flow to said heat transfer elements.

6. The heating and cooling pad of claim 1, wherein there is further provided a thermistor for controlling a flow of electrical power from an electrical power supply to said plurality of heat transfer elements whereby the temperature of said first planar surface is maintained within a predetermined range of temperatures.

7. The heating and cooling pad of claim 6, wherein there is further provided a shutoff means for deactivating the heating and cooling pad when the temperature of said first planar surface exceeds a predetermined maximum temperature.

8. A flexible heating and cooling pad for animal and human body parts comprising:

thermoelectric means having heating and cooling modes of operation for selectably providing a heating or a cooling effect;

a heat sink for transferring heat with respect to said thermoelectric means;

first and second planar surfaces made of flexible material and having side insertions disposed between and connecting said planar surfaces, said side insertions having at least two opposing portions made of semi-rigid mesh material, wherein said planar surfaces and side insertions define an enclosure for housing said thermoelectric means, wherein said thermoelectric means include a plurality of thermoelectric modules each having a first side attached to said first planar surface and a second side attached to said heat sink, said modules being interconnected to one another and adapted to be connected to a power source;

a fan located in the enclosure and proximate to one of said side insertions, said fan having directional fins for directing air flow to said thermoelectric means and said heat sink;

attachment means for releasably attaching the heating and cooling pad to a body part;

a thermistor having an electrical characteristic that varies with a temperature of said first planar surface;

shutoff means for discontinuing an electrical energy to said thermoelectric means in response to said thermistor; and a rheostat coupled electrically to said thermoelectric means for determining a range of temperature operation of said thermoelectric means.

9. The flexible heating and cooling pad of claim 8 wherein said first planar surface is impregnated with thermal conductive material for distributing heat therethrough.

* * * * *